United States Patent
Yoshiara et al.

(10) Patent No.: US 8,460,192 B2
(45) Date of Patent: Jun. 11, 2013

(54) ULTRASOUND IMAGING APPARATUS, MEDICAL IMAGE PROCESSING APPARATUS, DISPLAY APPARATUS, AND DISPLAY METHOD

(75) Inventors: Hiroki Yoshiara, Otawara (JP); Naohisa Kamiyama, Otawara (JP); Tetsuya Yoshida, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 782 days.

(21) Appl. No.: 12/575,174

(22) Filed: Oct. 7, 2009

(65) Prior Publication Data

US 2010/0094133 A1    Apr. 15, 2010

(30) Foreign Application Priority Data

Oct. 15, 2008   (JP) .................. 2008-266230

(51) Int. Cl.
*A61B 8/00*   (2006.01)
(52) U.S. Cl.
USPC ............ 600/437; 600/407; 600/441; 600/447
(58) Field of Classification Search
USPC ................... 600/437, 407, 441, 447
See application file for complete search history.

(56) References Cited

U.S. PATENT DOCUMENTS

| 6,582,370 B2 * | 6/2003 | Jibiki | 600/455 |
|---|---|---|---|
| 7,302,850 B2 | 12/2007 | Kamiyama | |
| 2001/0056236 A1 * | 12/2001 | Angelsen | 600/458 |
| 2008/0262354 A1 | 10/2008 | Yoshida et al. | |

FOREIGN PATENT DOCUMENTS

| CN | 101170947 A | 4/2008 |
|---|---|---|
| JP | 2714329 | 10/1997 |
| JP | 2000-333956 | 12/2000 |
| JP | 3495710 | 11/2003 |
| JP | 2004-321688 | 11/2004 |
| JP | 2007-330764 | 12/2007 |

OTHER PUBLICATIONS

U.S. Appl. No. 13/074,459, filed Mar. 29, 2011, Yoshida, et al.
U.S. Appl. No. 13/152,675, filed Jun. 3, 2011, Yoshiara, et al.
Chinese Office Action issued Aug. 3, 2012 in Patent Application No. 200910206345.1.
Office Action mailed Apr. 2, 2013 in Japanese Applicaton No. 2008-266230 filed Oct. 15, 2008 (w/English translation).

* cited by examiner

*Primary Examiner* — Unsu Jung
*Assistant Examiner* — Joel Lamprecht
(74) *Attorney, Agent, or Firm* — Oblon, Spivak, McClelland, Maier & Neustadt, L.L.P.

(57) ABSTRACT

An imaging part scans a predetermined site of a subject to which a contrast agent has been administered, with ultrasound waves, and thereby acquires plural frames of ultrasound image data. A contrast agent inflow detector detects the inflow of the contrast agent into each region based on the signal intensity in each region represented in the plural frames of ultrasound image data. A reference time determining part determines, as a reference time, a time point when the contrast agent inflow detector detects the inflow of the contrast agent into a first region of interest. A color coding part obtains a relative time of the inflow of the contrast agent into each region with reference to the reference time, and generates image data representing the color of each region with a hue corresponding to the relative time. An image based on the image data representing the hue is displayed.

21 Claims, 7 Drawing Sheets

COLOR CODING USING TIME OF
ARRIVAL OF CONTRAST AGENT t=0     t=t1     t=t2

FIG. 7B

COLOR CODING USING HEART RATE
UNTIL ARRIVAL OF CONTRAST AGENT

0TH         1ST         2ND
HEARTBEAT  HEARTBEAT  HEARTBEAT

ULTRASOUND IMAGING APPARATUS, MEDICAL IMAGE PROCESSING APPARATUS, DISPLAY APPARATUS, AND DISPLAY METHOD

BACKGROUND OF THE INVENTION

1. Field of the Invention

The present invention relates to an ultrasound imaging apparatus that, in a contrast echo method using an ultrasound contrast agent, presents, as diagnosis information, relative time information regarding the inflow of the ultrasound contrast agent in a region where the inflow of the ultrasound contrast agent is comparatively rapid and the other region. Further, the present invention relates to a medical image processing apparatus, a display apparatus, and a display method.

2. Description of the Related Art

An ultrasound diagnosis makes it possible to obtain a real time display of beats of the heart and movements of a fetus by a simple operation of applying an ultrasound probe to a body surface. Since an ultrasound diagnosis is highly safe, it is possible to repeatedly execute tests. Further, a system for an ultrasound diagnosis is smaller in scale than other diagnosis apparatuses, such as an X-ray diagnostic device, an X-ray Computed Tomography (CT) apparatus, and a Magnetic Resonance Imaging (MRI) apparatus. Therefore, it is possible to move an ultrasound imaging apparatus to a patient's bedside to easily and conveniently execute a test at the bedside. There are various ultrasound imaging apparatuses equipped with different types of functions, and compact-sized ultrasound imaging apparatuses that can be carried with one hand have been developed. Besides, since an ultrasound diagnosis does not involve the effects of exposure as seen in an X-ray diagnosis and other types of diagnoses, it is possible to use in obstetrics, home medical care, etc.

Ultrasound contrast agents that are administered intravenously have been commercialized, and the "contrast echo method" has become common in an ultrasound diagnosis. The object of this method is to enhance blood-flow signals by injecting an ultrasound contrast agent from a vein when executing a test of the heart, the liver, etc., and to assess the dynamic state of the blood flow. For most kinds of ultrasound contrast agents, micro bubbles function as reflection sources. For example, a second-generation ultrasound contrast agent called "Sonazoid" is composed of micro bubbles containing perfluorobutane gas with phospholipid as shell. Use of this ultrasound contrast agent allows a stable observation of the circulating current of the ultrasound contrast agent with transmission ultrasound waves of low and medium sound pressures.

When imaging a diagnosis site (for example, a liver cancer) after administering an ultrasound contrast agent to a subject, it is possible to observe the increase and decrease of the signal intensity during the inflow and outflow of the ultrasound contrast agent that is circulated with the blood flow. There have been studies indicating that differences in these moment-to-moment changes in signal intensity enable a differential diagnosis of benignancy or malignancy of a mass lesion and a diagnosis of a diffuse disease, etc.

In contrast to mere morphological information, moment-to-moment changes in signal intensity as described above typically usually need to be recorded or interpreted as motion image data. In general, a longer period of time is required for interpretation.

Therefore, a method of mapping inflow time information of an ultrasound contrast agent to be observed in motion images onto a single still image has been proposed (for example, refer to Japanese Patent Publication No. 2714329, Japanese Patent Publication No. 3495710, and Japanese Unexamined Patent Application Publication No. 2004-321688). Such a method represents, with different hues, a difference in times when signals of an ultrasound contrast agent form a peak and allows grasp of the inflow time at each site in the cross sectional surface in a single view.

However, the mapping of the inflow times of the contrast agent according to the conventional techniques involves the following problems.

The first problem is that it is difficult to set a reference time (zero point) of the moment-to-moment change. For example, in the method described in the abovementioned Japanese Patent Publication No. 2714329, a 2D image is drawn with different colors by comparing previously obtained signal intensities and newly obtained signal intensities mainly in the power Doppler imaging. When the ultrasound probe is moved three-dimensionally, it looks as if the previously obtained signals exist in the background because of the color changes due to the moment-to-moment changes. On the other hand, when the ultrasound probe is fixed, it is possible to represent, with different hues, the moment-to-moment changes of the signals due to the inflows of the ultrasound contrast agent. However, the abovementioned color changes are irrelevant to the time of administration of the ultrasound contrast agent, and it is therefore difficult to recognize, only based on the colors, absolute or relative time information, such as arrival times of the ultrasound contrast agent. In many implemented examples, a time to start injection of an ultrasound contrast agent from the vein is often set as the reference time. However, in this configuration, a difference in transmission time as the ultrasound contrast agent passes from the veins through the heart, the lungs, the heart and the arteries to an organ to be observed is also taken into consideration. Therefore, use of the value of the measurement result is not preferable as moment-to-moment changes of the organ being observed.

The second problem involves minor variation included in the measurement results. In the method described in the abovementioned Japanese Patent Publication No. 3495710, by applying different colors to two or more blood vessels having different peak values of the signals of the ultrasound contrast agent, for example, the artery and the portal vein can be identified and displayed. As in the method described in the abovementioned Japanese Patent Publication No. 2714329, this method may be applicable to relatively thick vascular systems.

However, in the actual contrast echo method, it is necessary to compare the inflow time of the ultrasound contrast agent into the entire tumor and the inflow time of the ultrasound contrast agent into the hepatic parenchyma (healthy part) around the tumor and other regions.

For example, when mapping the arrival times of the ultrasound contrast agent to the hepatic parenchyma that appears in an image, it is anticipated that the coloring is a mosaic pattern because the arrival times of the ultrasound contrast agent are not the same in all regions of the hepatic parenchyma. The mean value of these values or the degree of variation (dispersion) may be diagnostically significant. For such a diagnosis of a micro blood flow, it is difficult to favorably present diagnosis information by the method described in Japanese Patent Publication No. 3495710.

Further, according to the method described in the abovementioned Japanese Unexamined Patent Application Publication No. 2004-321688, it is possible to present the arrival time of the ultrasound contrast agent by executing more detailed operations based on a theoretical model of the circulating current of a micro blood flow.

However, it is difficult to solve the abovementioned first and second problems by the method described in Japanese Unexamined Patent Application Publication No. 2004-321688.

SUMMARY OF THE INVENTION

An object of the present invention is to provide an ultrasound imaging apparatus, a medical image processing apparatus, a display apparatus, and a display method, by which it is possible to present the relative inflow times of an ultrasound contrast agent between plural regions in an easily visible manner.

A first aspect of the present invention is an ultrasound imaging apparatus, having: an imaging part configured to acquire plural frames of ultrasound image data by scanning a predetermined site of a subject to which a contrast agent has been administered, with ultrasound waves; a contrast agent inflow detector configured to detect the inflow of said contrast agent to each region based on the signal intensity in said each region represented in said plural frames of ultrasound image data; a reference time determining part configured to determine, as a reference time, a time point when said contrast agent inflow detector has detected the inflow of said contrast agent to a first region of interest set within said scan range; a color coding part configured to obtain a relative time when said contrast agent has flowed into said each region with reference to said reference time, and to generate image data representing the color of said each region with a hue corresponding to said relative time; and a display controller configured to display an image based on said image data representing said hue, on a display.

According to the first aspect, by displaying the relative time when the ultrasound contrast agent flows into each region with different hues with reference to a region where a region of interest has been set, it is possible to present, in an easily visible manner, the differences in relative inflow times of the ultrasound contrast agent in plural regions. In this way, the operator can easily grasp the differences in relative inflow times of the ultrasound contrast agent in plural regions.

Further, a second aspect of the present invention is a medical image processing apparatus, comprising: a storage configured to store plural frames of ultrasound image data acquired by scanning, with ultrasound waves, a predetermined site of a subject to which a contrast agent has been administered; a contrast agent inflow detector configured to detect the inflow of said contrast agent into said each region based on the signal intensity in said each region represented in said plural frames of ultrasound image data; a reference time determining part configured to determine, as a reference time, a time point when said contrast agent inflow detector has detected the inflow of said contrast agent to a first region of interest set within said scan range; a color coding part configured to obtain a relative time when said contrast agent has flowed into said each region with reference to said reference time, and to generate image data representing the color of said each region with a hue corresponding to said relative time; and a display controller configured to display an image based on said image data representing said hue, on a display.

Further, a third aspect of the present invention is a display apparatus configured to, with reference to a time of detection of the inflow of a contrast agent to a first region of interest set in a cross section scanned with ultrasound waves, display a time of the inflow of said contrast agent to a second region of interest, which is different from said first region of interest, with a hue.

Further, a fourth aspect of the present invention is a display method for displaying, with reference to a time of detection of the inflow of a contrast agent to a first region of interest set in a cross section scanned with ultrasound waves, a time of the inflow of said contrast agent to a second region of interest, which is different from said first region of interest, with a hue.

Further, a fifth embodiment of the present invention is a display apparatus configured to display, with hues, relative inflow times of a contrast agent to a first region of interest and a second region of interest that are set on an ultrasound image.

Further, a sixth aspect of the present invention is a display method for displaying, with hues, relative inflow times of a contrast agent to a first region of interest and a second region of interest that are set on an ultrasound image.

Further, a seventh aspect of the present invention is an ultrasound imaging apparatus, comprising: a part configured to set a first region of interest and a second region of interest on an ultrasound image; a part configured to detect the inflow of a contrast agent to said first region of interest and said second region of interest; a part configured to execute color coding of the relative result of said detection regarding the inflow of said contrast agent to said first region of interest and said second region of interest; and a part configured to display the result of said color coding.

DETAILED DESCRIPTION OF THE EMBODIMENTS

Figure 1:
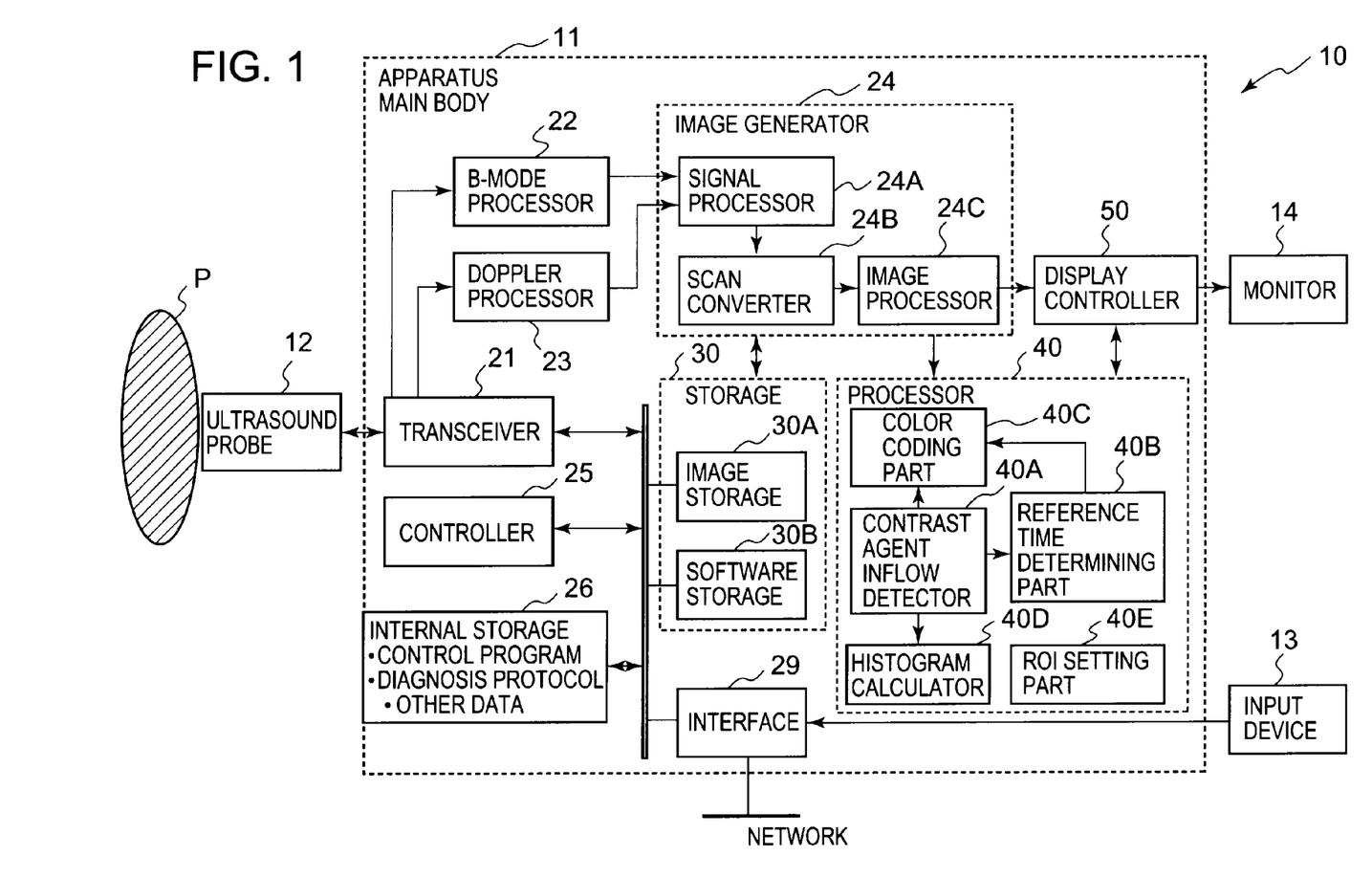
FIG. 1 is a block diagram showing an ultrasound imaging apparatus according to an embodiment of the present invention.

An ultrasonic imaging apparatus according to an embodiment of the present invention will be described with reference to FIG. 1. FIG. 1 is a block diagram showing an ultrasound imaging apparatus according to the embodiment of the present invention. In the following description, components having substantially the same functions and configurations are denoted by the same reference numerals.

An ultrasound imaging apparatus 10 according to this embodiment includes an ultrasound probe 12, an apparatus main body 11, an input device 13, and a monitor 14. The apparatus main body 11 includes a transceiver 21, a B-mode processor 22, a Doppler processor 23, an image generator 24, a controller 25, an internal storage 26, an interface 29, a storage 30, a processor 40, and a display controller 50.

The transceiver 21 and so on installed in the apparatus main body 11 may be configured by hardware such as an integrated circuit, or may be configured by a software modularized program.

The ultrasound probe 12 includes a plurality of ultrasound transducers, an acoustic matching layer disposed in the ultrasound transducer, and a backing material. The plurality of ultrasound transducers generate ultrasound waves based on a driving signal from the transceiver 21, convert the waves reflected from a subject P into electrical signals, and output the signals to the transceiver 21. The backing material prevents ultrasound waves from propagating backward from the ultrasound transducer. When ultrasound waves are transmitted from the ultrasound probe 12 to the subject P, the transmitted ultrasound waves are successively reflected on a surface with discontinuous acoustic impedance in the body tissue and received as echo signals by the ultrasound probe 12. The amplitude of the echo signals depends on differences in acoustic impedance of the discontinuous surface where the transmitted waves are reflected. When the transmitted ultrasound pulse is reflected on a moving blood flow or on the surface of a cardiac wall or the like, the echoes undergo frequency shift depending on the speed component in the ultrasound transmission direction of the moving object by the Doppler Effect. For the ultrasound probe 12, a 1D array probe in which a plurality of ultrasound transducers are arranged in line may be used, or a 2D array probe in which a plurality of ultrasound transducers are arranged two-dimensionally may be used.

The input device 13 includes a trackball, various switches, buttons, a mouse, a keyboard and so on, which are not shown in the drawings. The input device 13, which is connected to the apparatus main body 11, receives various instructions from the operator, conditions, an instruction to set a region of interest (ROI), an instruction to set image quality conditions, etc., and outputs them to the apparatus main body 11.

The monitor 14 displays morphological information and blood-flow information of a living body based on video signals from the image generator 24.

The transceiver 21 includes a pulsar circuit, a delay circuit, and a trigger generating circuit, which are not shown in the drawings. The pulsar circuit repeatedly generates a rate pulse for forming transmission ultrasound waves at a predetermined rate frequency fr (Hz) (frequency: 1/fr second). The delay circuit provides each rate pulse with a delay time necessary for focusing ultrasound waves into a beam for each channel and determining the transmission directivity.

The trigger generating circuit applies a driving pulse to the ultrasound probe 12 at a timing based on the rate pulse.

The transceiver 21 has a function of instantly changing the transmission frequency, the transmission drive voltage, and so on in accordance with an instruction from the controller 25. To be specific, change of the transmission drive voltage is executed by a linear amplifier type of transmission circuit capable of instantly switching the voltage value or by a mechanism of electrically switching a plurality of power units.

The transceiver 21 also includes an amplifier circuit, an A/D converter, and an adder, which are not shown in the drawings. For each channel, the amplifier circuit amplifies echo signals inputted via the ultrasound probe 12. The A/D converter provides the amplified echo signals with a delay time necessary for determining the reception directivity. The adder adds the echo signals provided with the delay time. Based on this addition, reflected components from a direction corresponding to the reception directivity are enhanced, and a comprehensive beam of ultrasound transmission and reception is formed based on the reception directivity and the transmission directivity.

The B-mode processor 22 receives the echo signals from the transceiver 21 and executes logarithmic amplification and envelope detection on the echo signals, thereby generating data in which the signal intensity is represented by the level of luminance. This data is transmitted to the image generator 24 and displayed on the monitor 14 as a B-mode image that represents the intensity of reflected waves by luminance.

The Doppler processor 23 extracts the blood flow, tissues and contrast agent echo components due to the Doppler effect by executing frequency analysis on the echo signals received from the transceiver 21 and obtains the blood-flow information such as the mean velocity, dispersion and power. The obtained blood-flow information is transmitted to the image generator 24 and displayed in color on the monitor 14 as a mean velocity image, a dispersion image, a power image, or a combined image thereof.

The image generator 24 generates ultrasound image data as a display image by converting a signal line obtained by scan with ultrasound waves into a signal line of a general video format, such as that of a television. The image generator 24 includes a memory for storing image data. For example, after diagnosis, in accordance with an instruction by the operator, the image data recorded during a test can be read out from the memory. The data before inputted into the image generator 24 may be referred to as "raw data."

The image generator 24 includes a signal processor 24A, a scan converter 24B, and an image processor 24C. The signal processor 24A performs filtering to determine the image quality at the level of a scanning line in the scan with ultrasound waves. An output from the signal processor 24A is transmitted to the scan converter 24B and stored in the image storage 30A. The scan converter 24B generates ultrasound image data as a display image by converting the signal line of the scanning line obtained by the scan with ultrasound waves into the signal line of the scanning line of the general video format, and outputs the data to the image processor 24C. The image processor 24C executes image processing such as luminance adjustment, contrast adjustment and space filtering on the ultrasound image data and composes ultrasound image data from data such as textual information of various setting parameters and scales. The image processor 24C then outputs the ultrasound image data to the display controller 50 as video signals. The display controller 50 displays an ultrasound image based on the ultrasound image data on the monitor 14. Thus, a cross-sectional image that represents the shape of tissues of the subject is displayed on the monitor 14. The ultrasound image data (cross-sectional image data) generated by the scan converter 24B and the ultrasound image data on which image processing has been executed by the image processor 24C may be stored in the image storage 30A.

The ultrasound probe 12, the transceiver 21, the B-mode processor 22, and the image generator 24 configure one example of the "imaging part" according to the present invention.

The controller 25 has a function as an information processing device and controls the operation of the apparatus main body 11. For example, the controller 25 is configured by a CPU (Central Processing Unit), reads out a control program for executing transmission and reception of ultrasound waves, image generation, image display, etc., temporarily stores the program into a software storage 30B, and executes operation, control, etc., relating to various processes.

The internal storage 26 stores a control program for executing transmission and reception of ultrasound waves, image generation and image display, information including a patient ID and a doctor's comment, diagnosis protocol, transmission and reception conditions, and other data. The internal storage 26 may also store the image data stored in the image storage 30A. The data stored in the internal storage 26 can also be transferred to an external device via the interface 29.

The interface 29 is an interface for the input device 13, a network, and an external storage device that is not shown in the drawings. Data such as ultrasound image data obtained by the ultrasound imaging apparatus 10 and analysis results can be transferred to another device by the interface 29 via the network.

The image storage 30A stores the image data received from the image generator 24. This image data can be read out in accordance with the operator's instruction after diagnosis and played as a still image or as a motion image by using plural frames of image data. The image storage 30A may also store signals outputted from the transceiver 21 (referred to as "RF (radio frequency) signals"), other raw data, image data acquired via the network, etc.

(Diagnosis Information Extracting Function)

In the present embodiment, imaging with ultrasound waves is performed under a condition that an ultrasound contrast agent is administered to a subject P. The diagnosis information extracting function described in the abovementioned Japanese Unexamined Patent Application Publication No. 2004-321688 allows extraction of diagnosis information that includes a blood-flow image (a blood-flow image including capillary vessels) and the histological physical quantity of the blood flow obtained from the blood-flow image. As described in Japanese Unexamined Patent Application Publication No. 2004-321688, by using a luminance holding operation such as a maximum value holding process and a weighting updating process executed on the temporally consecutive plural frames of ultrasound image data, it is possible to trace the movement of a single microbubble of the contrast agent. As a result, it is possible to visualize the structure of the fine blood vessel. Besides, as described in the abovementioned Japanese Patent Publication No. 2714329 and Japanese Patent Publication No. 3495710, it is possible to display, with different hues, blood vessels and tissues into which the ultrasound contrast agent flows at different times. This color coding process allows visual recognition of a time interval to which certain luminance in a finally displayed image belongs, by displaying with different colors for each time interval designated by the operator in advance.

According to the color coding process, it is possible, even when executing the luminance value holing operation such as the maximum value holding process and the weighting updating process, to provide a blood-flow image including the capillary vessel level of information in a state that the operator can easily observe without losing time information.

In clinical practice, it may be desired to set a plurality of regions of interest in a cross section scanned with ultrasound waves and grasp differences in relative arrival times of the ultrasound contrast agent among the plurality of regions of interest. For example, it may be desired to grasp differences in relative arrival times of the ultrasound contrast agent between the liver and the kidney, or differences in relative arrival times of the ultrasound contrast agent between the hepatic tumor and the hepatic parenchyma. In the color coding process described in Japanese Patent No. 2714329 and Japanese Patent No. 3495710, the operator sets a reference time (t=0) for displaying with hues in advance. Therefore, in the results of the color coding process, differences in relative arrival times of the targeted regions of interest may be hard to grasp. For example, even if there is a difference of five seconds in arrival time between an inflow time t1 to the renal parenchyma and an inflow time t2 to the hepatic parenchyma, the result may be (t1, t2)=(8, 13) or may be (t1, t2)=(15, 20), depending on the reference times set by the operator. Since the display with hues of the related art thus depends on the absolute values of time, the hue of each region of interest varies depending on the absolute values of time, and therefore, it is difficult and complicated to read out information indicating "time difference of five seconds" from the display.

(Setting of Region of Interest)

Figure 2:
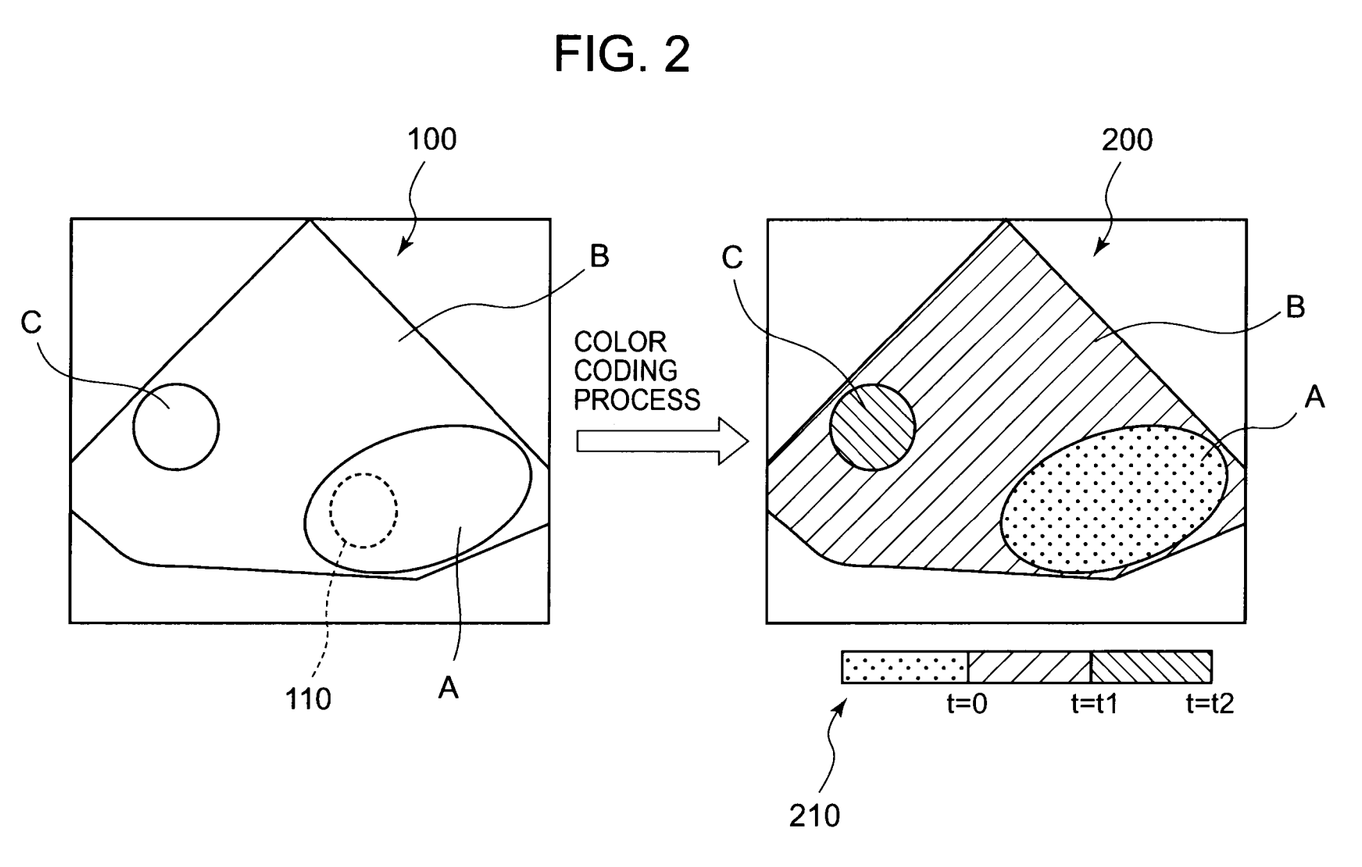
FIG. 2 is a view for describing the setting of a region of interest and a color coding process.

Therefore, in the present embodiment, relative arrival times of the ultrasound contrast agent between the respective regions are obtained and a color coding process is performed based on the relative arrival times. Firstly, the display controller 50 displays, on the monitor 14, an ROI marker representing a region of interest (ROI) so as to be superimposed on a cross-sectional image. The operator can move the ROI marker to any position on the cross-sectional image by using the input device 13. An example of the setting of the ROI marker will be described with reference to FIG. 2. FIG. 2 is a view for describing the setting of the region of interest and the color coding process. When the image generator 24 generates cross-sectional image data, the display controller 50 displays a cross-sectional image 100 based on the cross-sectional image data, on the monitor 14. The display controller then displays, on the monitor 14, the ROI marker 110 for designating the region of interest so as to be superimposed on the cross-sectional image 100. The ROI marker 110 is shaped to enclose an arbitrary range.

The operator can move the ROI marker 110 to any position on the cross-sectional image 100 by using the input device 13, and can also change the shape of the ROI marker 110 to any shape. For example, in the case of observing a hepatic disease, the region of interest can be set in a large blood vessel such as the portal vein that is not affected by the disease or in another organ such as the renal parenchyma.

(Detection of Inflow of Ultrasound Contrast Agent into Region of Interest and Time to Start Color Coding)

When the subject P is imaged with ultrasound waves after administration of an ultrasound contrast agent thereto and plural frames of cross-sectional image data are generated by the image generator 24, the plural frames of cross-sectional image data are outputted to the display controller 50 and the processor 40. As shown in FIG. 2, the display controller 50 displays the respective frames of cross-sectional images 100 on the monitor 14 in the temporal order and displays the ROI marker 110 so as to be superimposed on each of the cross-sectional images 100 on the monitor 14. The operator moves the ROI marker 110 to a desired position on the cross-sectional image 100 by using the input device 13. Coordinate information of the region of interest designated by the ROI marker 110 is outputted from the display controller 50 to the processor 40.

Upon reception of the plural frames of cross-sectional image data and the coordinate information of the region of interest designated by the ROI marker, the processor 40 monitors the signal intensity (luminance value) of each pixel in the region of interest, thereby monitoring the inflow of the ultrasound contrast agent to the region of interest. Then, the processor 40 obtains the arrival time of the ultrasound contrast agent into the region of interest, and obtains the arrival time of the ultrasound contrast agent into other regions, assuming the arrival time into the region of interest as the reference time. That is to say, the processor 40 obtains the relative arrival time of the ultrasound contrast agent into each of the regions with reference to the arrival time of the ultrasound contrast agent into the region of interest. The processor 40 then converts the hue of each pixel of the cross-sectional image data into the hue corresponding to the relative arrival time, and the display controller 50 displays the image after the color coding on the monitor 14. The following is a description of the details of specific processes of the processor 40.

The processor 40 includes a contrast agent inflow detector 40A, a reference time determining part 40B, a color coding part 40C, a histogram calculator 40D, and an ROI setting part 40E.

Upon reception of the plural frames of cross-sectional image data obtained at different times from the image generator 24, the contrast agent inflow detector 40A monitors the signal intensity (luminance value) of each pixel, and detects a time point when the signal intensity is a preset threshold or more. The detected time point is equivalent to a time of the inflow of the ultrasound contrast agent to a region corresponding to each pixel. For example, assuming, as an initial time, a time point at which the ultrasound contrast agent is administered to the subject P and imaging is started, the contrast agent inflow detector 40A measures, for each pixel, a time between the initial time and a time point at which inflow of the ultrasound contrast agent is detected.

For example, when the operator gives an instruction to start imaging by using the input device 13 at the time of administering the ultrasound contrast agent to the subject P to start imaging, a time point at which the instruction is given is set as the initial time in the processor 40. The contrast agent inflow detector 40A measures the time between the initial time and the time point of detection of the inflow of the ultrasound contrast agent, as the arrival time of the ultrasound contrast agent to each pixel. The contrast agent inflow detector 40A outputs the coordinate information of each pixel and the time when the ultrasound contrast agent reaches each pixel (the arrival time) to the reference time determining part 40B, the color coding part 40C, and the histogram calculator 40D.

Figure 4A:
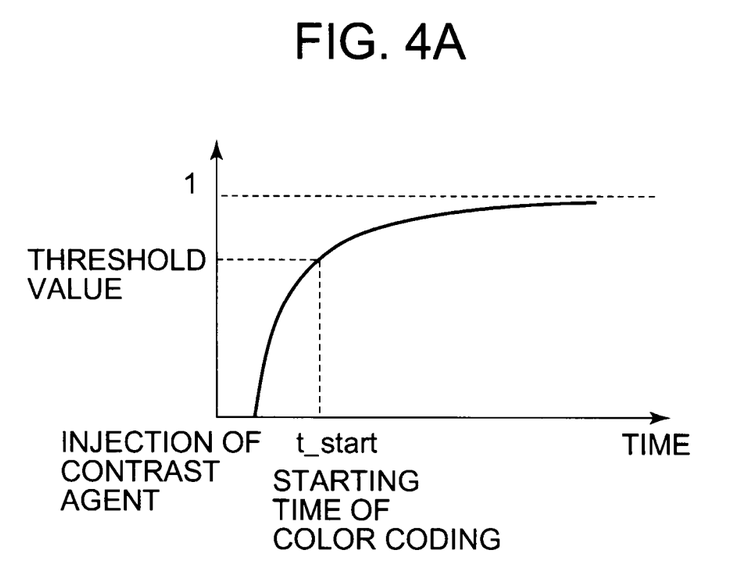
FIG. 4A is a graph showing a method for determining a reference time to start the color coding process.
Figure 4B:
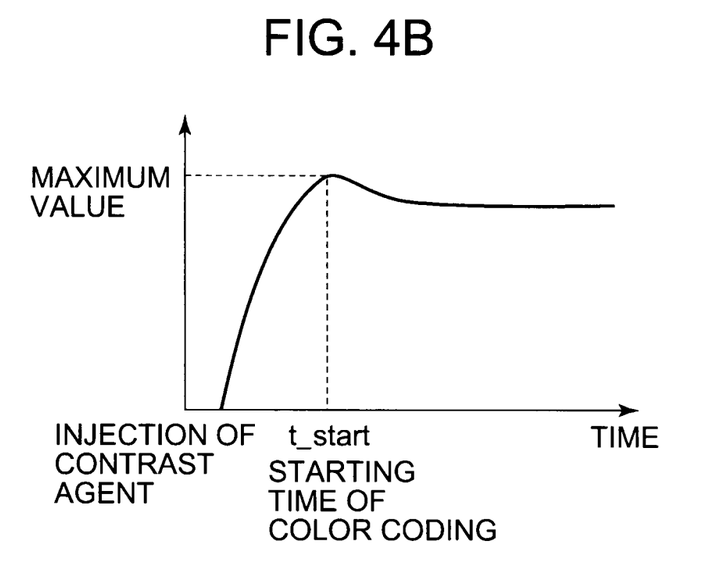
FIG. 4B is a graph showing a method for determining a reference time to start the color coding process.

The reference time determining part 40B monitors the pixels within the region of interest (ROI) in the cross-sectional image data of each frame, detects the number of pixels into which the ultrasound contrast agent has flowed in the regions of interest, and determines a reference time for starting the color coding process. A method of determining the reference time will be described below with reference to FIG. 4A and FIG. 4B. FIG. 4A and FIG. 4B are graphs showing the method of determining the reference time for starting the color coding process. For example, the reference time determining part 40B obtains the number of all of the pixels within the region of interest.

The reference time determining part 40B then receives the coordinate information of each pixel and the arrival time of the ultrasound contrast agent to each pixel, from the contrast agent inflow detector 40A, and obtains the proportion of pixels at which the ultrasound contrast agent has arrived from among all of the pixels within the region of interest. Then, as shown in FIG. 4A, the reference time determining part 40B obtains a time point when the proportion of pixels where the ultrasound contrast agent has arrived with respect to all of the pixels within the region of interest is a preset threshold (a predetermined proportion) or more, and determines a time point when the proportion reaches the threshold as the reference time for starting the color coding process. The reference time determining part 40B then outputs the reference time for starting the color coding process to the color coding part 40C.

Alternatively, the reference time determining part 40B may obtain the mean value of the signal intensity (the luminance value) of all of the pixels within the region of interest and determine the reference time based on the mean value. For example, as shown in FIG. 4B, the reference time determining part 40B may determine a time point when the mean value of the signal intensity of all of the pixels within the region of interest reaches the maximum value, as the reference time for starting the color coding process. Alternatively, the reference time determining part 40B may determine a time point when the mean value of the signal intensity reaches a preset threshold, as the reference time for starting the color coding process.

(Color Coding Process)

The color coding part 40C receives the coordinate information of each pixel and the arrival time of the ultrasound contrast agent to each pixel from the contrast agent inflow detector 40A, receives the reference time from the reference time determining part 40B, and obtains a relative arrival time when the ultrasound contrast agent has flowed into each region corresponding to each pixel with reference to the reference time. That is to say, assuming the reference time as zero, the color coding part 40C obtains the relative arrival time when the ultrasound contrast agent has flowed into each region corresponding to each pixel. The color coding part 40C then converts the hue of each pixel in the cross-sectional image data into a hue corresponding to the relative arrival time. The color coding part 40C outputs the cross-sectional image data after the color coding to the display controller 50. The display controller 50 displays a cross-sectional image after the color coding on the monitor 14. For example, a conversion table in which relative arrival times and hues are linked is previously set in the color coding part 40C. Referring to the conversion table, the color coding part 40C determines the hues corresponding to the relative arrival times and converts the hue of each pixel.

FIG. 2 shows an image on which the color coding process has been executed. For example, assuming the reference time as time t=0, the color coding part 40C converts the hue of pixels where the arrival time is included in a first time interval (t=0 or less) into red, converts the hue of pixels where the arrival time is included in a second time interval (t=0 to t1) into green, and converts the hue of pixels where the arrival time is included in a third time interval (t=t1 to t2) into blue. The display controller 50 displays a cross-sectional image 200 with the hue converted on the monitor 14. Consequently, a region A in which the region of interest is set (for example, the kidney) is displayed with a reference hue (red), and other regions (such as the liver) are displayed with hues corresponding to the relative times of arrival of the ultrasound contrast agent. For example, in the cross-sectional image 200, a region B different from the region A is displayed in green, and a region C is displayed in blue. Besides, the display controller 50 may display a color bar 210 representing the relation between the relative arrival times and the hues.

By thus displaying the relative arrival time of the ultrasound contrast agent to each region with a hue with reference to the region A (e.g., the kidney) in which the region of interest is set, it becomes easier to visually recognize a difference in relative time of arrival of the ultrasound contrast agent between the reference region A and another region (e.g., the liver). Consequently, the operator can easily, quantitatively grasp clinically necessary diagnosis information.

Figure 3:
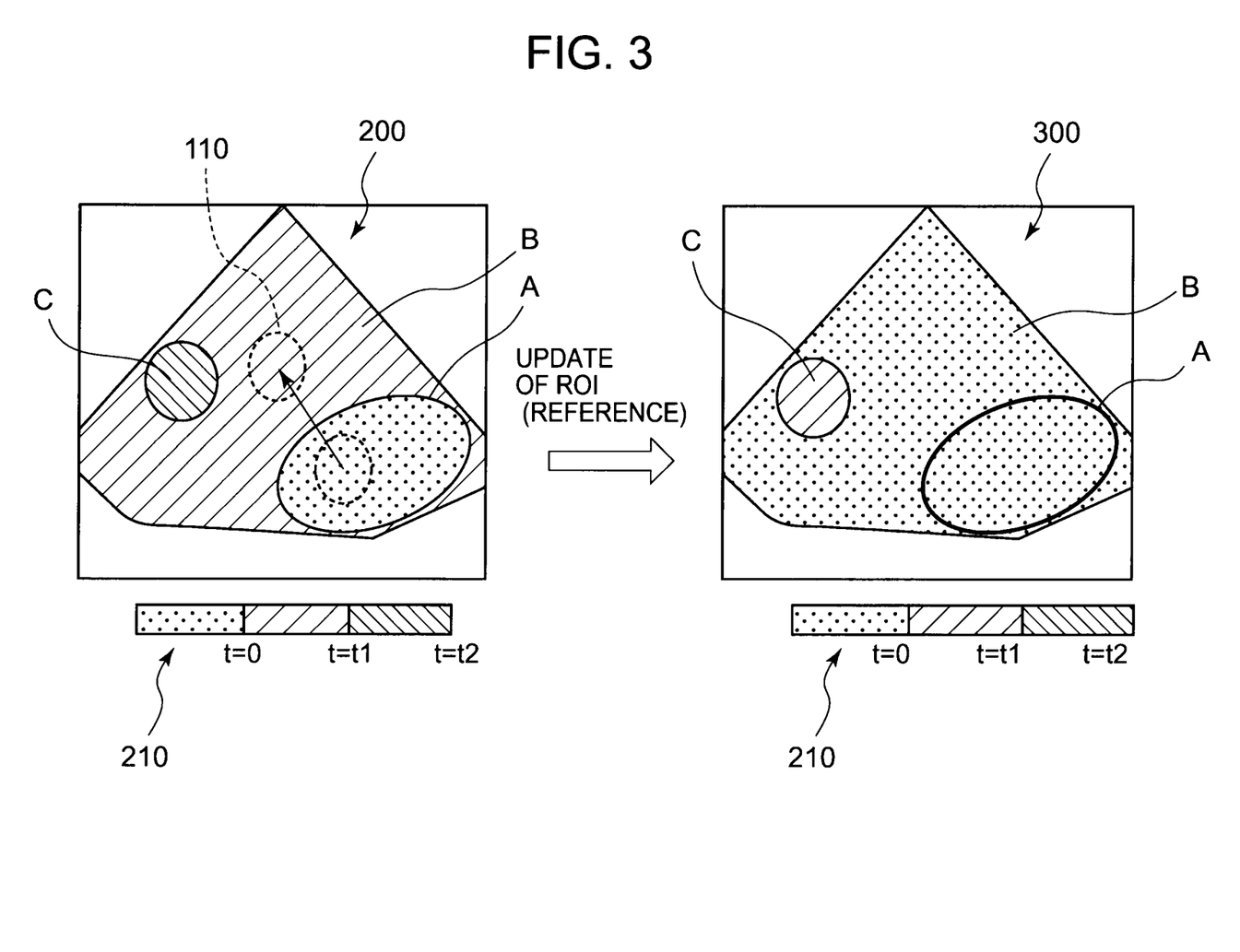
FIG. 3 is a view for describing the setting of a region of interest and a color coding process.

After image data is acquired, the color coding process may be executed with a position to set the region of interest changed. A case of changing the setting position of the region of interest will be described with reference to FIG. 3. FIG. 3 is a view for describing the setting of the region of interest and the color coding process. As shown in FIG. 3, in a state that the cross-sectional image 200 after the color coding process is displayed on the monitor 14, the operator moves an ROI marker 110 to a desired position by using the input device 13.

In an example shown in FIG. 3, the ROI marker 110 is moved from the region A into the region B. Consequently, the region of interest is newly set within the region B and the coordinate information of the newly set region of interest is outputted to the processor 40.

As in the abovementioned process, the reference time determining part 40B monitors the pixels within the region of interest in the cross-sectional image data of each frame, detects the number of pixels into which the ultrasound contrast agent has flowed in the region of interest, and determines the reference time for starting the color coding process. In the example shown in FIG. 3, the reference time determining part 40B obtains a time point when the proportion of pixels at which the ultrasound contrast agent has arrived to all of the pixels within the region of interest set in the region B reaches a threshold (a predetermined proportion), and determines the time point when the proportion reaches the threshold as the reference time.

Alternatively, the reference time determining part 40B may determine, as the reference time, a time point when the mean value of the signal intensity (the luminance value) of all of the pixels in the region of interest set in the region B reaches the maximum value or when the mean value reaches a threshold.

The color coding part 40C obtains the relative arrival time when the ultrasound contrast agent has flowed into each region corresponding to each pixel with reference to the newly obtained reference time. That is to say, assuming the newly obtained reference time as zero, the color coding part 40C obtains the relative arrival time when the ultrasound contrast agent has flowed into each region corresponding to each pixel.

The color coding part 40C then converts the hue of each pixel in the cross-sectional image data into a hue corresponding to the newly obtained relative arrival time.

The display controller 50 displays a cross-sectional image after the new color coding on the monitor 14. Thus, when the setting position of the region of interest is changed from the region A to the region B, the arrival time of the ultrasound contrast agent detected in the changed region of interest is set as the new reference time, and each region is subjected to color coding and displayed with reference to the new reference time. For example, as shown in FIG. 3, a cross-sectional image 300 after the new color coding is displayed on the monitor 14.

Since the time of arrival of the ultrasound contrast agent into the region B to which the newly set region of interest belongs is included in the first time interval (t=0 or less), the color coding part 40C converts the hue of the pixels within the region B into red. Thus, the region B is displayed in red. Regarding the region A in which the time of arrival of the contrast agent is earlier than in the region B, the hue may be unchanged without the color coding, the hue may be converted into red as in the reference region B, or the hue may be converted into another hue as a negative time and displayed.

For example, the color coding part 40C compares the arrival time of the ultrasound contrast agent to each pixel with the reference time, and converts the hue of the pixels at which the ultrasound contrast agent arrives at an earlier time than the reference time into the hue (red) corresponding to the first time interval (t=0 or less). In the example shown in FIG. 3, the color coding part 40C converts the hue of the region A at which the ultrasound contrast agent arrives at an earlier time than the reference time, into red. Consequently, the region A is converted into red and displayed. Alternatively, the color coding part 40C may compare the time of arrival of the ultrasound contrast agent to each pixel with the reference time and convert the hue of the pixels at which the ultrasound contrast agent arrives at an earlier time than the reference time into another hue (e.g., yellow) as a negative time.

By the abovementioned method, it becomes easier to visually recognize a difference in relative time of arrival of the ultrasound contrast agent between the region of interest (reference region) set at an arbitrary position in a scanning cross section and the other region.

As a result, it becomes possible to easily provide clinically useful diagnosis information. That is to say, since the operator can observe hues converted based on a relative time relation between regions instead of hues converted based on the absolute value of time, the operator can easily recognize a difference in relative time of arrival of the ultrasound contrast agent. Consequently, it is possible to easily grasp a difference in relative time of arrival of the ultrasound contrast agent to targeted organs.

Instead of performing color coding based on the arrival time of the ultrasound contrast agent to each region, color coding may be performed by obtaining a time when the signal intensity (luminance value) due to inflow of the ultrasound contrast agent reaches the maximum value. In this case, the contrast agent inflow detector 40A receives the cross-sectional image data of each frame, monitors the signal intensity (luminance value) in each pixel, and detects a time point when the signal intensity reaches the maximum (maximum intensity time) for each pixel. The reference time determining part 40B obtains a time point when the proportion of pixels where the signal intensity (luminance value) reaches the maximum among all of the pixels in the region of interest reaches a preset threshold (a predetermined proportion) and determines the time point as the reference time. The color coding part 40C obtains, for each pixel, a relative maximum intensity time at which the signal intensity (luminance value) in each pixel reaches the maximum with reference to the reference time. That is to say, assuming the reference time as zero, the color coding part 40C obtains, for each pixel, the relative maximum intensity time when the signal intensity reaches the maximum. The color coding part 40C then converts the hue of each pixel in the cross-sectional image data into a hue corresponding to the relative maximum intensity time. By thus executing color coding based on the time when the signal intensity reaches the maximum, the operator can easily grasp a relative time difference in inflow of the ultrasound contrast agent between plural regions.

Although this embodiment describes a color coding process using three time intervals as an example, the color coding process may be executed using any number of time intervals.

(Quantification Using Histogram of Inflow Time)

Based on an image obtained by the abovementioned color coding process, differences in contrast agent arrival time among plural regions of interest may be quantitatively obtained. For example, differences in times of arrival of the ultrasound contrast agent among the kidney, the liver and a hepatic disease site are obtained as numerical values. All of the times of arrival of the ultrasound contrast agent to a comparatively broad region such as organ parenchyma are not necessarily uniform throughout the organ. In a case that the arrival times vary depending on locations even in a single site, displayed colors look like a mosaic.

Therefore, it is difficult to intuitively grasp the relative arrival times. Besides, information whether the times of arrival of the ultrasound contrast agent are comparatively uniform or variable may also contribute to distinguishing whether a diffuse disease or a tumor is benignant or malignant. Thus, it is useful to easily present the mean value and the variance value of the time of arrival of the ultrasound contrast agent in a certain region.

Figure 5:
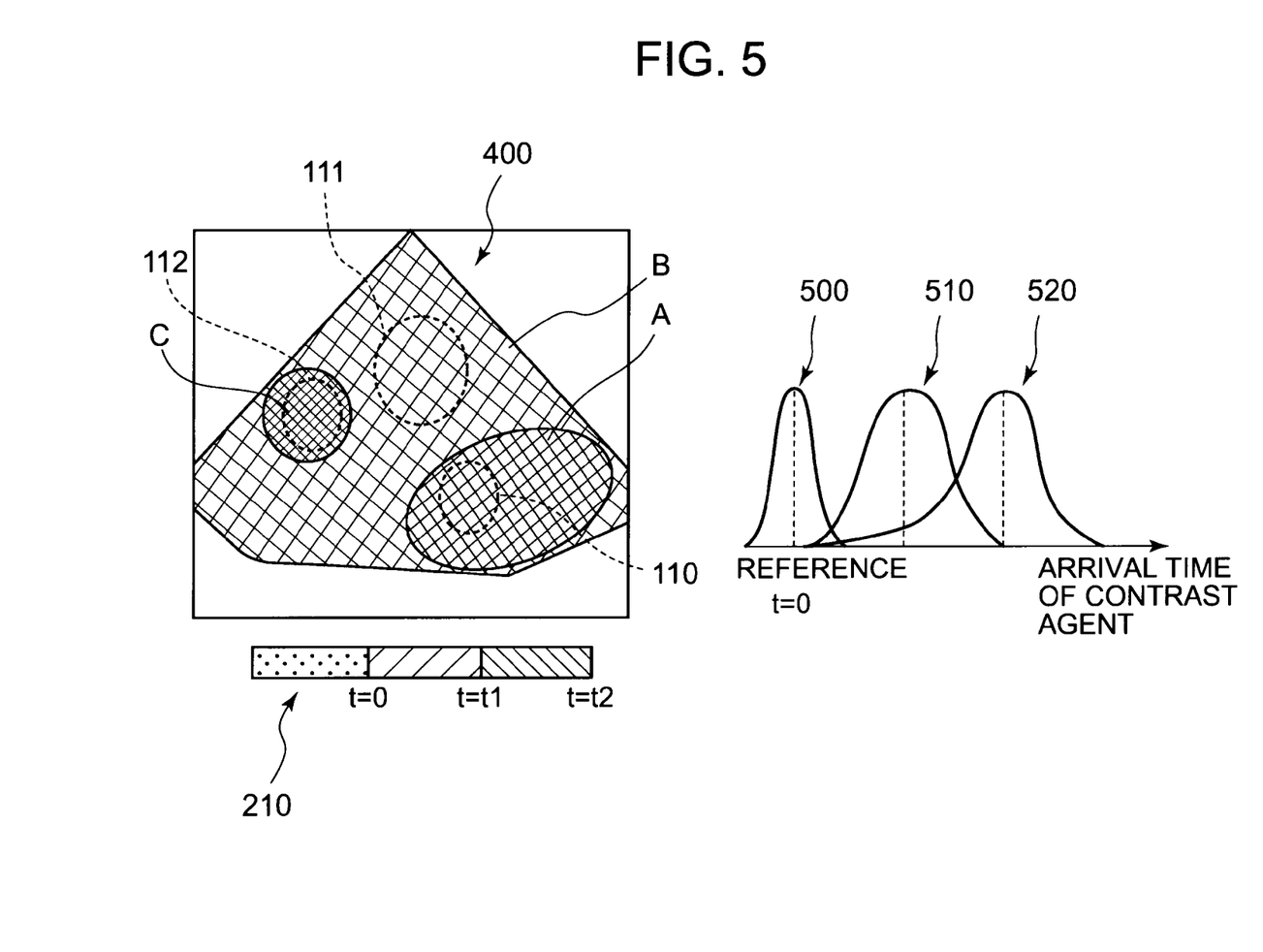
FIG. 5 is a view showing a cross-sectional image on which plural regions of interest are set and the frequency distribution of an inflow time of an ultrasound contrast agent in each of the regions of interest.

In the present embodiment, plural regions of interest are set in an arbitrary position on the cross-sectional image. A case of setting three regions of interest will be described below with reference to FIG. 5. FIG. 5 is a view showing a cross-sectional image in which plural regions of interest are set and a frequency distribution of times of inflow of the ultrasound contrast agent in each of the regions of interest.

For example, as shown in FIG. 5, the display controller 50 displays a cross-sectional image 400 on the monitor 14. The display controller 50 further displays, on the monitor 14, ROI markers 110, 111 and 112 for setting the regions of interest, so as to be superimposed on the cross-sectional image 400. The operator moves the ROI markers 110, 111 and 112 to desired positions by using the input device 13, thereby setting the regions of interest in three positions. For example, by moving the ROI marker 110 into the region A, moving the ROI marker 111 into the region B, and moving the ROI marker 112 into a region C, a region of interest is set in each of the regions. Coordinate information of the regions of interest designated by the ROI markers 110, 111 and 112, respectively, are outputted from the display controller 50 to the processor 40.

The histogram calculator 40D of the processor 40 receives the coordinate information of each pixel and the time of arrival of the ultrasound contrast agent to each pixel from the contrast agent inflow detector 40A, and obtains the frequency distribution of the pixels with respect to the time of arrival of the ultrasound contrast agent. That is, the histogram calculator 40D obtains a histogram that indicates the frequency distribution of pixels with respect to the times of arrival of the ultrasound contrast agent. For example, the histogram calculator 40D obtains a histogram that indicates the frequency distribution of pixels with respect to the times of arrival of the ultrasound contrast agent based on the times of arrival of the ultrasound contrast agent to each pixel included in a first region of interest a designated by the ROI marker 110. In the same manner, the histogram calculator 40D obtains a histogram indicating the frequency distribution of pixels with respect to the times of arrival of the ultrasound contrast agent based on the times of arrival of the ultrasound contrast agent to each pixel included in a second region of interest 13 designated by the ROI marker 111. In the same manner, the histogram calculator 40D obtains a histogram indicating the frequency distribution of pixels with respect to the times of arrival of the ultrasound contrast agent based on the times of arrival of the ultrasound contrast agent to each pixel within a third region of interest γ designated by the ROI marker 112. Thus, when the frequency distribution of pixels with respect to the times of arrival of the ultrasound contrast agent to each region of interest is obtained, the display controller 50 displays the frequency distribution 500, the frequency distribution 510, and the frequency distribution 520 of the pixels. In FIG. 5, the horizontal axis shows the time of arrival of the ultrasound contrast agent and the longitudinal axis shows the frequency distribution of pixels.

The histogram calculator 40D may obtain a time of the mode value (the peak value), a time of the median point of the frequency distribution, or the variance based on the frequency distribution of pixels with respect to the times of arrival of the ultrasound contrast agent and determine the time of the peak value or the time of the median point as the time of arrival of the ultrasound contrast agent. For example, the histogram calculator 40D obtains the time of the peak value for the frequency distribution 500 and determines the time as the time of arrival of the contrast agent to the first region of interest α. In the same manner, the histogram calculator 40D obtains the time of the peak value for the frequency distribution 510 and determines the time as the time of arrival of the contrast agent to the second region of interest 13. In the same manner, the histogram calculator 40D obtains the time of the peak value for the frequency distribution 520 and determines the time as the time of arrival of the contrast agent to the third region of interest γ. The display controller 50 displays, on the monitor 14, the time of the peak value for each frequency distribution as the time when the ultrasound contrast agent has arrived. The histogram calculator 40D may obtain the time of the median point and the variance for each frequency distribution, and the display controller 50 may display the time of the median point and the variance on the monitor 14.

The histogram calculator 40D may obtain differences in times of arrival of the ultrasound contrast agent to each region of interest obtained from the peak value and the median point for the frequency distribution. For example, in a case that the time of arrival of the ultrasound contrast agent to the first region of interest α is the fastest, the histogram calculator 40D determines the time of arrival obtained from the frequency distribution 500 relating to the first region of interest α, as the reference time. The histogram calculator 40D then obtains the difference between the time of arrival to the first region of interest α and the time of arrival to the second region of interest 13, and also obtains the difference between the time of arrival to the first region of interest α and the time of arrival to the third region of interest γ. The display controller 50 then displays the differences in arrival times between the regions of interest, on the monitor 14.

By thus obtaining the frequency distribution relating to each of the regions of interest, it is possible to quantitatively evaluate the differences in time of arrival of the ultrasound contrast agent in each site. For example, by setting the first region of interest a in the kidney, the second region of interest β in the liver, and the third region of interest γ in the hepatic disease site, it becomes possible to quantitatively grasp the differences in time of arrival of the ultrasound contrast agent in each of the sites.

There is a case that the region of interest includes a blood vessel into which the ultrasound contrast agent comparatively rapidly flows, and parenchyma into which the ultrasound contrast agent comparatively slowly flows. In this case, by manually moving the region of interest, changing the size of the region of interest, or adopting the mode value for the frequency distribution of the pixels, it is possible to reduce the effects of a region in which the degree of inflow is specifically different from the surrounding tissues, such as a blood vessel into which the ultrasound contrast agent comparatively rapidly flows.

During the color coding, the frequency distribution (histogram) may be displayed on the monitor 14 in real time. Although this embodiment describes a case of setting three regions of interest, any number of regions of interest may be set. In a case that the frequency distribution (histogram) is not obtained, the processor 40 may have no histogram calculator 40D. The histogram calculator 40D is equivalent to one example of the "distribution calculator" according to the present invention.

(Modification)

Although the Region of Interest is Manually Set in the Cross section scanned with ultrasound waves in the above-mentioned embodiment, the region of interest may be automatically set. The automatic setting of the region of interest is performed by the ROI setting part 40E of the processor 40. In the case of manually setting the region of interest, the processor 40 may have no ROI setting part 40E.

Figure 6:
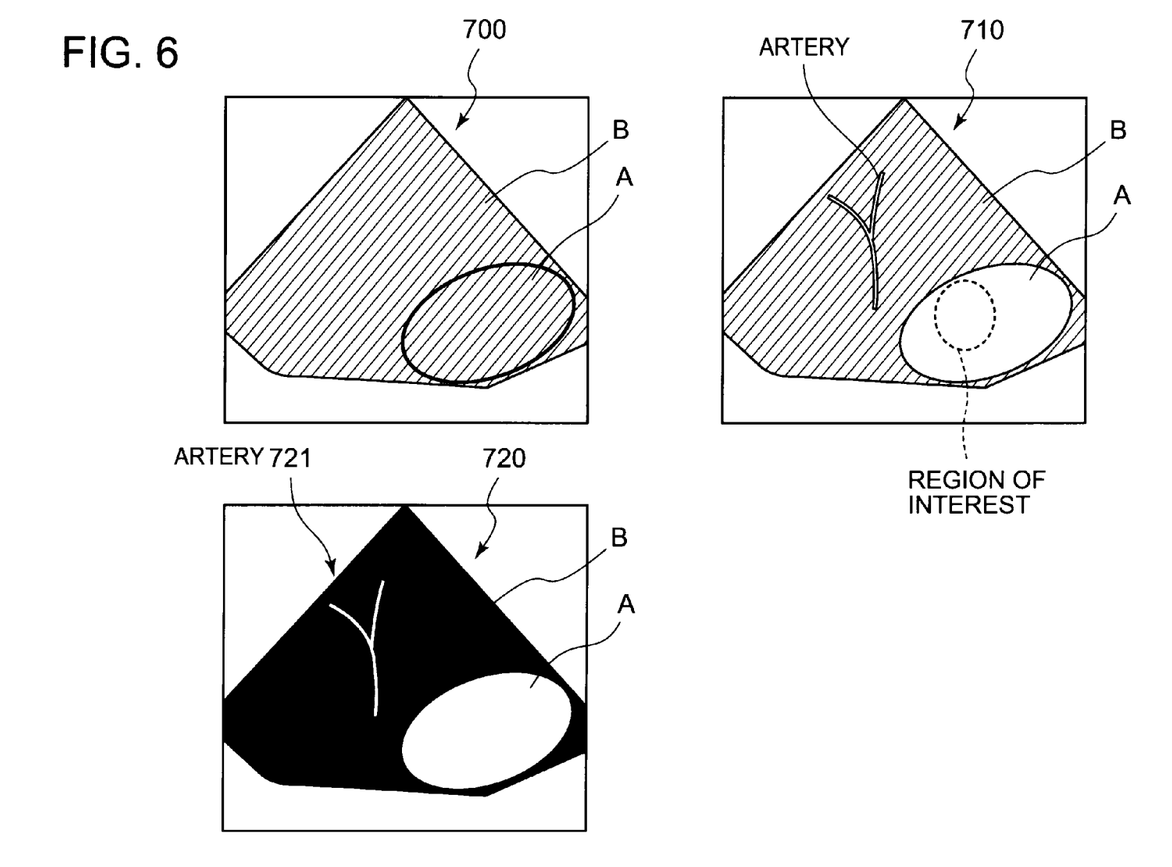
FIG. 6 is a view showing an image for describing a process of automatically setting the region of interest.

A process according to the modification will be described with reference to FIG. 6. FIG. 6 is a view showing an image for describing a process of automatically setting the region of interest.

The ROI setting part 40E receives plural frames of cross-sectional image data and obtains a difference between the consecutive frames, thereby generating difference image data. For example, as shown in FIG. 6, the ROI setting part 40E obtains a difference between a cross-sectional image 710 of the $(N+1)^{th}$ frame and a cross-sectional image 700 of the $N^{th}$ frame, thereby generating a difference image 720. Then, the ROI setting part 40E monitors, at each position, the signal intensity (luminance value) of pixels included in the region of interest while moving a preset region of interest (ROI) having a predetermined size at predetermined intervals on the difference image 720. To be specific, the ROI setting part 40E detects pixels in which the signal intensity (luminance value) reaches a threshold from among the pixels in the region of interest. That is to say, the ROI setting part 40E determines that the ultrasound contrast agent has flowed into a region corresponding to the pixels with the signal intensity reaching the threshold, and detects the pixels at which the signal intensity reaches the threshold. Consequently, the ROI setting part 40E detects regions into which the ultrasound contrast agent has flowed within the region of interest.

Then, the ROI setting part 40E gradually moves the region of interest on the difference image 720 and specifies, on the difference image 720, a position where the proportion of pixels with the signal intensity reaching the threshold in the region of interest reaches a predetermined position of all of the pixels in the region of interest. For example, the ROI setting part 40E specifies the position where the proportion of pixels with the signal intensity reaching the threshold in the region of interest reaches 80% of all pixels in the region of interest.

The ROI setting part 40E sets the region of interest to a position where the proportion reaches the predetermined proportion. For example, in a case that, in the region A, the proportion of pixels at which the signal intensity reaches the threshold in the region of interest reaches 80% of all pixels in the region of interest, the ROI setting part 40E sets the region of interest in the region A.

By obtaining the frequency distribution of the pixels with respect to the luminance values in the region of interest, a position to set the region of interest may be specified. In this case, the ROI setting part 40E monitors the signal intensities (luminance values) of the pixels included in the region of interest while gradually moving the preset region of interest having a predetermined size on the difference image 720. Then, the ROI setting part 40E obtains the frequency distribution of the pixels with respect to the luminance values. Then, the ROI setting part 40E specifies a site where the proportion of pixels where the luminance value reaches a threshold in the region of interest reaches a predetermined proportion (for example, 80%), and sets the region of interest to that site.

The region of interest may be automatically set based on the cross-sectional image data of each frame without using a difference image.

To be specific, the ROI setting part 40E detects pixels where the signal intensities (luminance values) reaches a threshold from among the pixels in the region of interest while gradually moving the region of interest having a predetermined size on the cross-sectional image of each frame. Thus, the ROI setting part 40E detects a region into which the ultrasound contrast agent has flowed in the region of interest. Then, the ROI setting part 40E specifies a site where the proportion of pixels where the signal intensities reaches a threshold in the region of interest reaches a predetermined proportion (for example, 80%) among all of the pixels in the region of interest, and sets the region of interest to the site.

The ROI setting part 40E may obtain the frequency distribution of pixels with respect to the luminance values while moving the region of interest having a predetermined size on the cross-sectional image of each frame. The ROI setting part 40E then specifies a site where the proportion of pixels where the luminance value is a threshold or more in the region of interest is the predetermined proportion or more, and sets the region of interest to the site.

As in the abovementioned embodiment, after automatically setting the region of interest as described above, by executing determination of the reference time and the color coding process, a cross-sectional image with hue converted is generated and displayed.

A range to move the region of interest on an image may be limited. For example, the operator specifies a desired range for specifying the region of interest on the image by using the input device 13. The ROI setting part 40E receives the coordinate information of the range designated by the operator, specifies a site where the proportion of pixels where the signal intensity is a threshold or more in the region of interest is a predetermined proportion or more while gradually moving the region of interest within the designated range, and specifies the region of interest to the site. By thus limiting the range to move the region of interest for specifying the region of interest, it is possible to reduce the time taken for specifying the region of interest.

The region of interest may be set by another method. For example, to set the region of interest in the kidney, where the ultrasound contrast agent flows throughout the entire organ comparatively rapidly, the ROI setting part 40E sets a region of interest in a region having a first size where a difference value equal to or more than a threshold in a difference image is closely distributed.

For example, the ROI setting part 40E sets the region of interest in a region where the proportion of pixels at which the signal intensity is the threshold or more is the predetermined proportion or more (for example, 80%), the region of interest having the first size. The region of interest is thus set in the kidney.

On the other hand, to set the region of interest in the liver, where the inflow of the ultrasound contrast agent is comparatively slower than in the kidney and the ultrasound contrast agent flows in from blood vessels such as arteries, the ROI setting part 40E sets the region of interest in a region where a difference value equal to or more than a threshold in the difference image is distributed within a smaller area than the distribution in the kidney. For example, the ROI setting part 40E sets the region of interest in a region where the proportion of pixels at which the signal intensity is the threshold or more is the predetermined proportion or more, the region of interest having a second size that is smaller than the first size. In this way, the region of interest is set in the liver.

Besides, for the liver, it is sometimes desired to set the region of interest in the hepatic parenchyma by avoiding blood vessels such as arteries. In such cases, the ROI setting part 40E can set the region of interest in the liver instead of a detected artery 721 having been detected. As the difference value for the artery 721 is the threshold or more, the region of interest can be set to avoid positions that exceed the threshold.

The region of interest may be set automatically by utilizing anatomical information based on a fundamental-wave image. For example, the ROI setting part 40E may receive cross-sectional image data, designate a specific organ such as the kidney and the liver by performing an image recognition process such as pattern matching, and set the region of interest in the organ. For example, when setting the region of interest in the kidney, the ROI setting part 40E specifies the kidney represented in the cross-sectional image through image recognition and sets the region of interest in the kidney.

After thus setting the region of interest automatically, as in the process according to the abovementioned embodiment, the reference time is determined and the color coding process is performed.

Besides, a histogram may be calculated, or the position of the region of interest may be changed.

(Parameters for Color Coding)

Figure 7A:
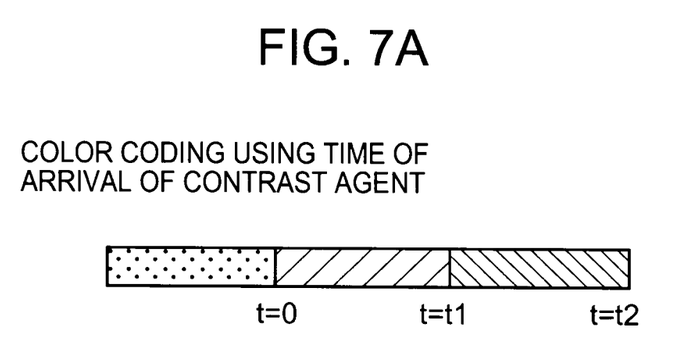
FIG. 7A is a view showing a parameter for the color coding.
Figure 7B:
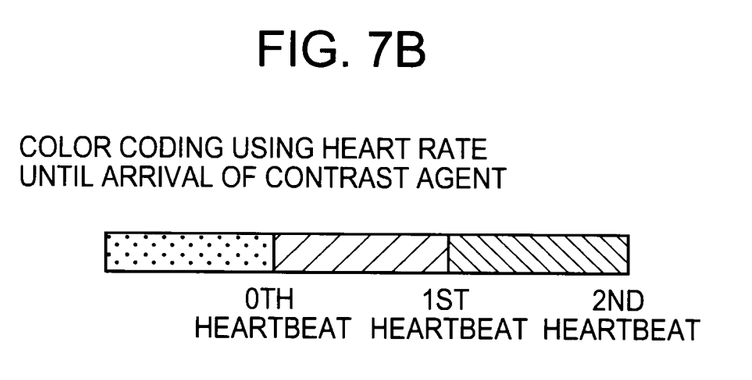
FIG. 7B is a view showing a parameter for the color coding.

Parameters for color coding will be described with reference to FIG. 7A and FIG. 7B. FIG. 7A and FIG. 7B are diagrams illustrating parameters for color coding. In the abovementioned embodiment, as shown in FIG. 7A, a relative arrival time of the ultrasound contrast agent is used as a parameter for color coding. The parameter for color coding is not limited to the arrival time. For example, as shown in FIG. 7B, the hue of each pixel may be converted by using the number of heartbeats until the ultrasound contrast agent reaches each region as a parameter. For example, an electrocardiograph may be used to acquire an electrocardiogram of the subject P. The color coding part 40C assumes the heartbeat acquired at the reference time as the zero heartbeat. Then, with reference to the zero heartbeat the color coding part 40C converts the hue of pixels at which the arrival time is included in a first heart rate interval (0 heartbeat or less) into red, converts the hue of pixels at which the arrival time is included in a second hear rate interval (0 to 1 heartbeat) into green, and converts the hue of pixels at which the arrival time is included in a third heart rate interval (1 to 2 heartbeats) into blue. The display controller 50 displays a cross-sectional image with hue converted on the monitor 14.

Instead of using an electrocardiograph, the heartbeats may be specified based on the periodic movements of the tissues represented in the image. For example, the color coding part 40C specifies 1 period to be 1 heartbeat based on the movements of the periodically moving tissues represented in the cross-sectional image data. In addition, the heartbeats may be specified from the blood-flow information. For example, the heartbeats may be specified by obtaining Doppler information, or the heartbeats may be specified based on the pulsation of the blood vessels.

The processor 40 includes an information processor (CPU) and a storage device such as a ROM (Read Only Memory), RAM (Random Access Memory), and HDD (Hard Disk Drive) that are not shown. The storage device stores processing programs for executing the functions of each part of the processor 40. The processing program includes a contrast-agent inflow detecting program for executing the functions of the contrast agent inflow detector 40A, a reference-time determining program for executing the functions of the reference time determining part 40B, a color coding program for executing the functions of the color coding part 40C, a histogram calculating program for executing the functions of the histogram calculator 40D, and a region-of-interest setting program for executing the functions of the ROI setting part 40E.

When the information processor (CPU) executes each program, detection of the arrival time of the contrast agent, determination of the reference time, the color coding process, calculation of the frequency distribution (histogram), and automatic setting of the region of interest are executed. In addition, the display controller 50 includes an information processor (CPU) and a storage device. A display-control program for executing the functions of the display controller 50 is stored in the storage device. The information processor executes the display-control program to cause the monitor 14 to display a cross-sectional image and an image with hue converted.

(Medical Image Processing Apparatus)

The processes according to the abovementioned embodiment may be performed by using a medical image processing apparatus having the functions of the processor 40. This medical image processing apparatus includes the processor 40, the display controller 50, the monitor 14, and the input device 13. For example, by imaging a subject to which an ultrasound contrast agent has been administered by using an ultrasound imaging apparatus, plural frames of cross-sectional image data are obtained. The medical image processing apparatus receive the plural frames of cross-sectional image data from the ultrasound imaging apparatus and stores the plural frames of cross-sectional image data into the storage device. The medical image processing apparatus detects the arrival time of the ultrasound contrast agent, determines the reference time, and performs the color coding process based on the cross-sectional image data of these multiple frames and generates an image that represents the relative inflow information of the ultrasound contrast agent with different hues for display. The medical image processing apparatus may calculate the frequency distribution (histogram) of pixels relative to the arrival time of the contrast agent and set the region of interest automatically. In addition, as in the abovementioned ultrasound imaging apparatus 10, the use of such a medical image processing apparatus enables the operator to easily observe differences in the relative arrival times of the ultrasound contrast agent in plural regions.

What is claimed is:

1. An ultrasound imaging apparatus, comprising:
    an imaging part configured to acquire plural frames of ultrasound image data by scanning in a scan range predetermined regions of a subject to which a contrast agent has been administered, with ultrasound waves;
    a region of interest (ROI) designator configured to designate at least a first ROI within said scan range on an ultrasonic image derived from said ultrasound image data;
    a processor including,
    a contrast agent inflow detector configured to detect the inflow of said contrast agent to each region based on the signal intensity in said each region represented in said plural frames of ultrasound image data;
    a reference time determiner configured to determine, as a reference time, a time point when said contrast agent inflow detector has detected the inflow of said contrast agent based on an excess of the signal intensity over a threshold in each said region of interest designated within said scan range, and
    a color coder configured to determine a hue with reference to said reference time and the inflow of the contrast agent into said each region, and to generate image data representing the color of said each region with said hue; and
    a display controller configured to display an image based on said image data representing said hue, on a display.

2. The ultrasound imaging apparatus according to claim 1, wherein:
    said reference time determiner is configured to, when said first region of interest is set in another position within said scan range, receive the result of the detection by said contrast agent inflow detector, and to determine, as a new reference time, a time point when said contrast agent has flowed into said first region of interest set in said other position;

said color coder is configured to newly obtain a relative time when said contrast agent has flowed into said each region with reference to said new reference time, and to newly generate image data representing the color of said each region with a hue corresponding to said new relative time; and said display controller is configured to display an image based on said newly generated image data, on said display.

3. The ultrasound imaging apparatus according to claim 1, wherein:

said contrast agent inflow detector is configured to detect a time point when said signal intensity in said each region reaches a preset threshold as the inflow of said contrast agent to said each region;

said reference time determiner is configured to determine, as said reference time, a time point when said signal intensity in said first region of interest reaches a preset threshold; and said color coder is configured to obtain a relative time when said signal intensity in said each region reaches said preset threshold with reference to said reference time, and to generate said image data representing the color of said each region with a hue corresponding to said relative time.

4. The ultrasound imaging apparatus according to claim 1, wherein:

said contrast agent inflow detector is configured to detect a time point when said signal intensity in said each region reaches the maximum as the inflow of said contrast agent into said each region;

said reference time determiner is configured to determine, as said reference time, a time point when said signal intensity in said first region of interest reaches the maximum; and said color coder is configured to obtain a relative time when said signal intensity in said each region reaches the maximum with reference to said reference time, and to generate said image data representing the color of said each region with a hue corresponding to said relative time.

5. The ultrasound imaging apparatus according to claim 1, wherein:

said reference time determiner is configured to determine, as said reference time, a time point when the proportion of pixels where said contrast agent inflow detector has detected the inflow of said contrast agent within said first region of interest reaches a preset threshold.

6. The ultrasound imaging apparatus according to claim 1, wherein:

said reference time determiner is configured to determine, as said reference time, a time point when the mean value of said signal intensity in said first region of interest reaches the maximum.

7. The ultrasound imaging apparatus according to claim 1, further comprising:

a distribution calculator configured to, based on the result of the detection by said contrast agent inflow detector, detect a time point when said contrast agent has flowed into each pixel included in said first region of interest, obtain a first frequency distribution of the number of pixels with respect to an inflow time of said contrast agent to said each pixel included in said first region of interest, detect a time point when said contrast agent has flowed into each pixel included in a second region of interest set in a different position from said first region of interest, and obtain a second frequency distribution of the number of pixels with respect to an inflow time of said contrast agent to said each pixel included in said second region of interest, wherein said display controller is configured to display said first frequency distribution and said second frequency distribution on the display.

8. The ultrasound imaging apparatus according to claim 7, wherein:

said distribution calculator is configured to obtain a time when said first frequency distribution is the mode value or median point as the inflow time of said contrast agent to said first region of interest, to obtain a time when said second frequency distribution is the mode value or median point as the inflow time of said contrast agent to said second region of interest, and to obtain a difference between the inflow time to said first region of interest and the inflow time to said second region of interest; and said display controller is configured to display said difference in inflow time on said display.

9. The ultrasound imaging apparatus according to claim 1, further comprising an ROI setter configured to specify a site where the proportion of the number of pixels where said signal intensity is a preset threshold or more among all pixels within a range having a predetermined size is a predetermined proportion or more, and to set said first region of interest at said specified site.

10. The ultrasound imaging apparatus according to claim 1, further comprising an ROI setter configured to generate difference image data by obtaining a difference in luminance value between the frames for said plural frames of ultrasound image, to specify a site where the proportion of the number of pixels where said difference is a preset threshold or more from among all pixels within a range having a predetermined size in said difference image data is a predetermined proportion or more, and to set said first region of interest in said specified site.

11. The ultrasound imaging apparatus according to claim 1, further comprising an ROI setter configured to specify a specific site based on the morphology of tissue represented in the ultrasound image data, and to set said first region of interest in said specific site.

12. The ultrasound imaging apparatus according to claim 1, wherein, said color coder is configured to receive the heart rate of said subject, obtain a relative heart rate when said contrast agent has flowed into said each region with reference to said reference time, and to generate said image data representing the color of said each region with a hue corresponding to said relative heart rate.

13. A medical image processing apparatus, comprising:

a storage configured to store plural frames of ultrasound image data acquired by scanning, with ultrasound waves, a predetermined site of a subject to which a contrast agent has been administered;

a region of interest (ROI) designator part configured to designate at least a first ROI within said scan range on an ultrasonic image derived from said ultrasound image data, a processor including, a contrast agent inflow detector configured to detect the inflow of said contrast agent into said each region based on the signal intensity in said each region represented in said plural frames of ultrasound image data, a reference time determiner configured to determine, as a reference time, a time point when said contrast agent inflow detector has detected the inflow of said contrast agent based on an excess of the signal intensity over a threshold in each said region of interest designated within said scan range, and a color coder configured to determine a hue with reference to said reference time and the inflow of the contrast agent into said each region, and to generate image data representing the color of said each region with said hue; and a display controller configured to display an image based on said image data representing said hue, on a display.

14. The medical image processing apparatus according to claim 13, wherein:
said reference time determiner is configured to, when said first region of interest is set in another position within said scan range, receive the result of the detection by said contrast agent inflow detector, and to determine, as a new reference time, a time point when said contrast agent has flowed into said first region of interest set in said other position;
said color coder is configured to newly obtain a relative time when said contrast agent has flowed into said each region with reference to said new reference time, and to newly generate said image data representing the color of said each region with a hue corresponding to said new relative time; and
said display controller is configured to display an image based on said newly generated image data, on said display.

15. The medical image processing apparatus according to claim 13, wherein:
said contrast agent inflow detector is configured to detect a time point when said signal intensity in said each region reaches a preset threshold as the inflow of said contrast agent to said each region;
said reference time determiner is configured to determine a time point when said signal intensity in said first region of interest reaches a preset threshold, as said reference time; and
said color coder is configured to obtain a relative time when said signal intensity in said each region reaches a preset threshold with reference to said reference time, and to generate said image data representing the color of said each region with a hue corresponding to said relative time.

16. The medical image processing apparatus according to claim 13, wherein:
said contrast agent inflow detector is configured to detect a time point when said signal intensity in said each region reaches the maximum, as the inflow of said contrast agent to said each region;
said reference time determiner is configured to determine, as said reference time, a time point when said signal intensity in said first region of interest reaches the maximum; and
said color coder is configured to obtain a relative time when said signal intensity in said each region reaches the maximum with reference to said reference time, and to generate said image data representing the color of said each region with a hue corresponding to said relative time.

17. The medical image processing apparatus according to claim 13, wherein said reference time determiner is configured to determine, as said reference time, a time point when the proportion of the number of pixels at which said contrast agent inflow detector has detected the inflow of said contrast agent within said first region of interest reaches a preset threshold.

18. The medical image processing apparatus according to claim 13, wherein said reference time determiner is configured to determine, as said reference time, a time point when the mean value of said signal intensity in said first region of interest reaches the maximum.

19. The medical image processing apparatus according to claim 13, further comprising:
a distribution calculator configured to, based on the result of the detection by said contrast agent inflow detector, detect a time point when said contrast agent has flowed into each pixel included in said first region of interest, obtain a first frequency distribution of the number of pixels with respect to an inflow time of said contrast agent to said each pixel included in said first region of interest, detect a time point when said contrast agent has flowed into each pixel included in a second region of interest set in a different position from said first region of interest, and obtain a second frequency distribution of the number of pixels with respect to an inflow time of said contrast agent to said each pixel included in said second region of interest,
wherein said display controller is configured to display said first frequency distribution and said second frequency distribution on said display.

20. The medical image processing apparatus according to claim 19, wherein:
said distribution calculator is configured to obtain a time when said first frequency distribution is the mode value or median point as an inflow time of said contrast agent to said first region of interest, obtain a time when said second frequency distribution is the mode value or median point as an inflow time of said contrast agent to said second region of interest, and obtain a difference in inflow time for said first region of interest and said second region of interest; and
said display controller is configured to display said difference in inflow time, on said display.

21. An ultrasound imaging apparatus, comprising:
a region of interest (ROI) designator part configured to designate regions of interest within a scan range on an ultrasonic image derived from plural frames of ultrasound image data; and
a processor including,
a contrast agent inflow detector configured to detect inflow of a contrast agent to each region of interest based on the signal intensity in each said region of interest represented in said plural frames of ultrasound image data,
a reference time determiner configured to determine, as a reference time, a time point when said contrast agent inflow detector has detected the inflow of said contrast agent based on an excess of the signal intensity over a threshold in each said region of interest designated within said scan range, and
a color coder configured to determine a hue with reference to said reference time and the inflow of the contrast agent into said each region, and to generate image data representing the color of said each region with said hue; and
a display configured to display an image based on said image data representing said hue.

* * * * *